United States Patent [19]

Baugh

[11] Patent Number: 5,441,892
[45] Date of Patent: Aug. 15, 1995

[54] BLOOD CLOT MASS MEASURING TECHNIQUE

[75] Inventor: Robert F. Baugh, Parker, Colo.

[73] Assignee: Medtronic HempTec, Inc., Englewood, Colo.

[21] Appl. No.: 962,486

[22] Filed: Oct. 15, 1992

[51] Int. Cl.⁶ .......................................... G01N 33/86
[52] U.S. Cl. ...................... 436/69; 436/63; 436/174; 435/13; 73/64.41; 422/73
[58] Field of Search ............. 422/73; 436/63, 69, 436/86, 174; 435/13; 73/64.41

[56] References Cited

U.S. PATENT DOCUMENTS

| | | | |
|---|---|---|---|
| 3,302,452 | 2/1967 | Leslie | 73/64.43 |
| 3,307,392 | 2/1967 | Owen et al. | 73/64.43 |
| 3,525,254 | 2/1969 | Milanes | 73/64.1 |
| 3,854,324 | 12/1974 | Altshuler et al. | 73/64.42 |
| 3,963,349 | 6/1976 | Albright et al. | 73/64.41 |
| 4,000,972 | 1/1977 | Braun et al. | 436/69 |
| 4,026,671 | 5/1977 | Simons et al. | 422/73 |
| 4,040,788 | 8/1977 | Simons et al. | 436/34 |
| 4,058,367 | 11/1977 | Gilford | 422/63 |
| 4,074,971 | 2/1978 | Braun et al. | 436/69 |
| 4,081,242 | 3/1978 | Girolami | 73/54.01 |
| 4,285,906 | 8/1981 | Meltzer et al. | 422/64 |
| 4,390,499 | 6/1983 | Curtis et al. | 422/73 |
| 4,391,780 | 7/1983 | Boris | 422/102 |
| 4,443,408 | 4/1984 | Mintz | 422/73 |
| 4,533,519 | 8/1985 | Baugh et al. | 422/73 |
| 4,534,939 | 8/1985 | Smith et al. | 422/73 X |
| 4,551,308 | 11/1985 | Mintz | 422/58 |
| 4,599,219 | 7/1986 | Cooper et al. | 422/73 X |
| 4,612,801 | 9/1986 | Girolami | 73/64.1 |
| 4,663,127 | 5/1987 | Jackson et al. | 422/58 |
| 4,671,939 | 6/1987 | Mintz | 422/58 |
| 4,692,406 | 9/1987 | Becher et al. | 436/69 |
| 4,752,449 | 6/1988 | Jackson et al. | 422/73 |
| 4,782,026 | 11/1988 | Baugh et al. | 436/69 |
| 4,797,369 | 1/1989 | Mintz | 436/69 |
| 4,871,677 | 10/1989 | Baugh et al. | 436/69 |
| 4,960,694 | 10/1990 | Eckardt et al. | 436/69 |
| 4,986,964 | 1/1991 | Carr, Jr. et al. | 436/69 |
| 5,091,304 | 2/1992 | LaDuca et al. | 435/13 |
| 5,174,961 | 12/1992 | Smith | 422/73 |
| 5,314,826 | 5/1994 | Baugh | 436/69 |

OTHER PUBLICATIONS

Vander et al. "Human Physiology" 1985 p. 377.
Spivak Jerry "Fundamentals of Clinical Hemodology" 1984 pp. 390–391.
Brown Barbara, "Hematology: Principles and Procedures," 1980 pp. 126–127.
"Blood Component Therapy, A Physician's Handbook," American Association of Blood Banks, 1975.
J. Hirsh, M.D. and E. A. Brain, M.D., "Hemostasis & Thrombosis, a Conceptual Approach," Second Edition, pp. 1–45, 1983.

*Primary Examiner*—Donald E. Czaja
*Assistant Examiner*—Milton I. Cano
*Attorney, Agent, or Firm*—Ralph F. Crandell; Holland & Hart

[57] ABSTRACT

A clot mass condition of blood is evaluated by initially forming the clot in the sample of the blood and thereafter allowing the clot to condense. The initial formation of the clot is determined by measuring the drop time of a reciprocated indicator device upon which the clot is formed. The condensation of the clot is determined by measuring the stabilized and increased drop time of the indicator device after the initial clot formation has occurred. The clot mass is related to the quantity of fibrinogen in the blood sample which polymerizes in the clot. Clot condensation results in the clot being substantially only fibrinogen, so the stabilized condensation time is related to the fibrinogen concentration in the blood sample.

18 Claims, 5 Drawing Sheets

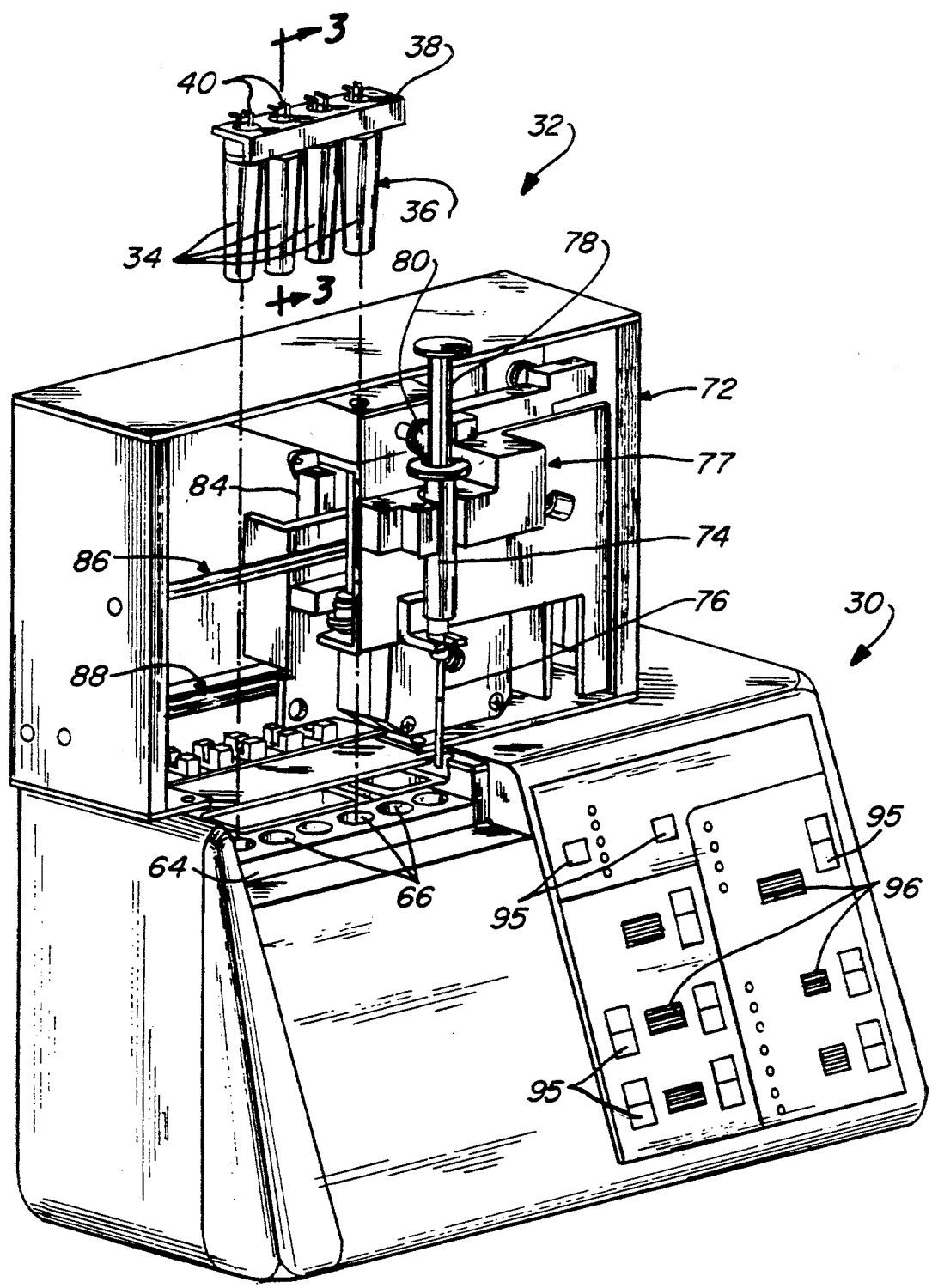
Fig_2

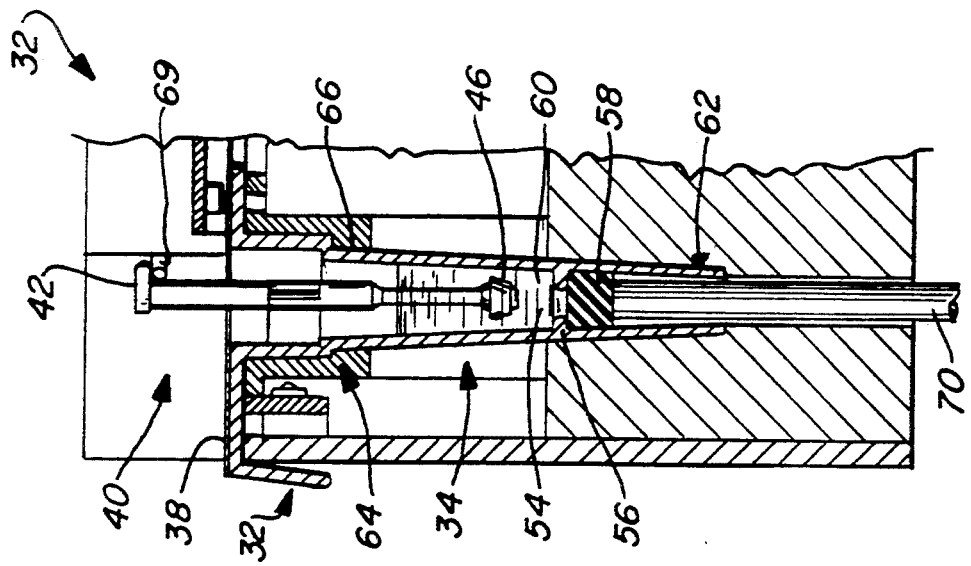
Fig_5
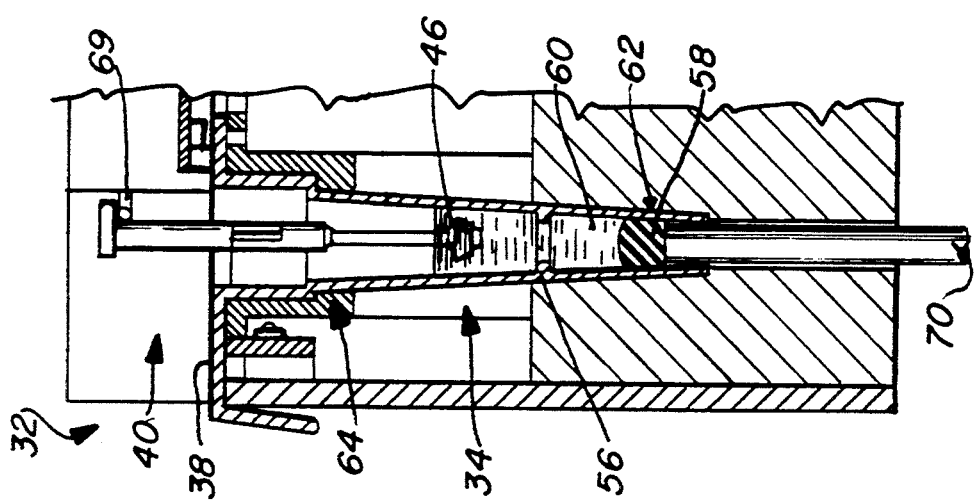
Fig_4
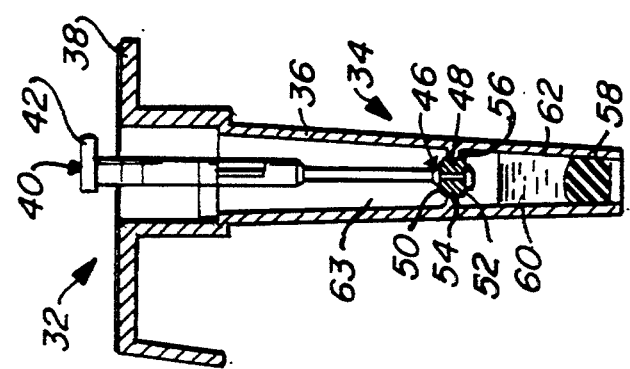
Fig_3

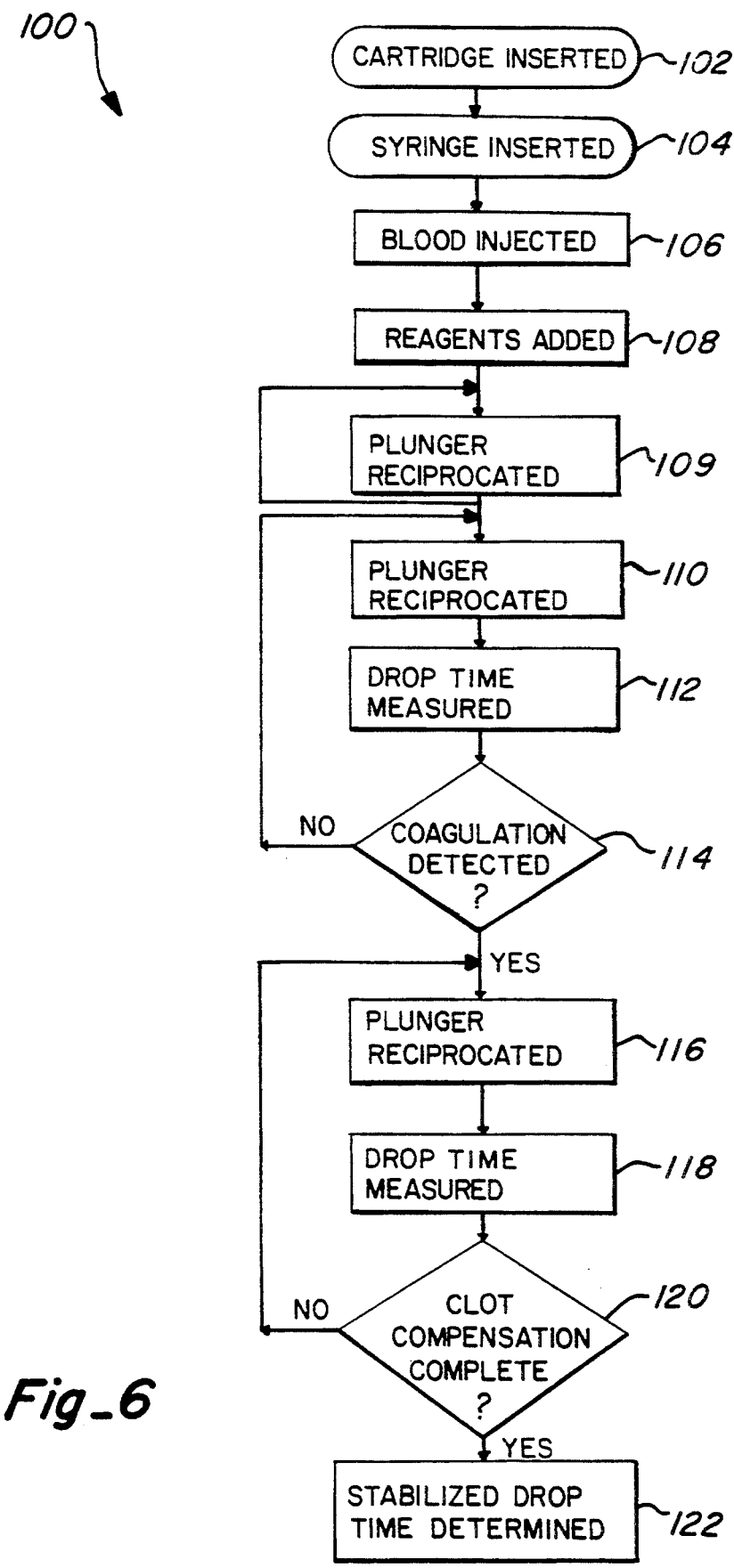
Fig_6

BLOOD CLOT MASS MEASURING TECHNIQUE

CROSS REFERENCE TO RELATED INVENTIONS

The invention described in this application is related to an invention for Blood Clot Lysis Measuring Technique, described in a patent application filed concurrently herewith, and to an invention for Platelet Activation and Function Evaluation Technique, described in application Ser. No. 07/749,211, filed Aug. 23, 1991 now U.S. Pat. No. 5,314,825, both of which are assigned to the assignee of the present invention. The disclosures of these prior applications are incorporated herein by this reference. The term "blood" as used herein may include whole blood and the separable components thereof, such as plasma and various concentrates.

FIELD OF THE INVENTION

This invention relates to a technique for measuring the mass of a blood clot in a blood or plasma sample. More particularly, this invention relates to a technique in which the amount of clottable material in a blood or plasma sample is evaluated. Even more particularly, the present invention relates to a technique in which the fibrinogen content of a whole blood or plasma sample is evaluated by measuring the mass of a clot of a fully clotted whole blood or plasma sample.

BACKGROUND OF THE INVENTION

Blood coagulation is a natural reparative process in which a blood clot is formed in response to blood or blood vessel trauma. Normally, blood contains platelets and other cells, as well as fibrinogen and other molecules, all of which circulate freely in the blood. However, in response to trauma to the blood or blood vessels, and in the absence of pathological or therapeutically induced conditions preventing some aspect of blood coagulation, the platelets agglutinate. As the platelets agglutinate, there is an increase in the concentration of the chemical thrombin in the blood. The thrombin has a proteolytic effect on the fibrinogen molecules circulating in the blood. This proteolytic activity results in the formation of fibrin monomers from the fibrinogen molecules. Then, in proximity to the surface of the agglutinated platelets, the fibrin monomers spontaneously polymerize into fibrin polymers. While the fibrin polymers are initially linked by hydrogen bonds, the fibrin is later stabilized by covalent bonds among the fibrin polymers resulting in a meshwork of fibrin polymers. This meshwork of fibrin polymers comprises the blood clot.

Unfortunately, any of a number of pathological and therapeutically induced conditions can prevent the formation of fibrin polymers. Fibrin polymers may fail to form because of coagulation problems, such as when there is a genetic defect limiting production of one or more required coagulation factors. Fibrin polymers may also fail to form if there is a deficiency of functioning platelets. Platelet concentrations may be deficient due to a failure of platelet production, to excessive platelet destruction or to excessive platelet storage in the spleen. If platelet concentrations are decreased, platelet agglutination will necessarily decrease. A decrease in platelet agglutination can limit the production of fibrin polymers by decreasing the available surface upon which the fibrin monomers can polymerize in the process leading to clot formation. Even if sufficient platelets are present, however, defects in platelet function can prevent the formation of fibrin polymers, such as when platelets do not synthesize or release required chemical reactants.

Of course when platelets and coagulation factors are present in normal concentrations and functioning adequately, fibrinogen must still be present in sufficient concentration if the polymerization of fibrinogen into fibrin is to occur. If there is no fibrinogen, fibrin monomers cannot be formed. In the absence of fibrin monomers, polymerization of fibrin cannot occur. Thus, the concentration of fibrinogen in a particular individual is directly related to that individual's potential for blood coagulation.

It could be helpful if physicians were able to better evaluate or determine a patient's potential for blood coagulation by measuring the patient's blood fibrinogen content. Knowledge of the blood fibrinogen content would allow physicians to more accurately pinpoint or eliminate excessive or inadequate blood fibrinogen levels as the cause of individual coagulation disorders. Furthermore, knowledge of fibrinogen content would also help avoid some surgical complications which might otherwise occur because of an excessive or inadequate concentration of blood fibrinogen of an individual undergoing surgery.

Currently, much detailed information about an individual's blood coagulation characteristics is available to aid physicians in the diagnosis of coagulation disorders and in the prevention of surgical and post-surgical coagulation complications. There are techniques currently available which measure coagulation times, coagulation factors, platelet function, fibrinolytic activity, the presence of circulating inhibitors, as well as other individual blood clotting characteristics. There is, however, no apparatus or method currently known which can rapidly and accurately quantify or evaluate fibrinogen levels.

It is against this background information that the below described significant improvements and advancements have taken place in the field of blood coagulation measurement.

SUMMARY OF THE INVENTION

The present invention relates to evaluating a condition of blood such as the mass of a clot or the fibrinogen content of the blood. The condition is evaluated by measuring the condensation of a clot of the blood. Condensation of the clot occurs after the clot is initially formed, and it is believed to result in part from expression of serum and other materials from the intermolecular spaces between fibrin monomers which are polymerizing into a meshwork which forms the clot. Upon the clot achieving a maximum degree of condensation, the clot is formed primarily of the fibrin polymers. The extent and fact of condensation therefore relates to the concentration of the fibrinogen in the blood sample that ultimately polymerizes into the clot meshwork. By measuring the clot condensation relative to the initially formed clot, the clot mass or the fibrinogen content may be evaluated.

The initial clotting condition and the maximum clot condensation condition are preferably measured by determining the drop or descent times of an indicator device which is repeatedly reciprocated through a sample of blood. The clot forms on the indicator device and slows its descent. The drop time of the indicator with an initially formed clot and the drop time of the indicator with a condensed clot are utilized to evaluate the condition. There is a rapid and almost instantaneous increase in drop time upon the initial formation of the clot, and the drop time stabilizes after a decrease from the initial clot formation drop time when the clot undergoes maximum condensation. Therefore both the initial clot formation drop time and the stabilized clot time are readily detected.

Another significant aspect of the present invention relates to measuring clot condensation on various dilutions of blood. The clot condensation measurements are then correlated to the concentrations to develop a mathematical or curvilinear relationship to evaluate the fibrinogen content of the blood based on the measurement of one sample.

A more complete appreciation of the present invention and its scope can be obtained from understanding the accompanying drawings, which are briefly summarized below, the following detailed description of presently preferred embodiments of the invention, and the appended claims.

DESCRIPTION OF DRAWINGS

FIG. 2 is a perspective view of a high sensitivity coagulation detection apparatus and a plunger sensor detection cartridge preferably used to obtain the information illustrated in FIG. 1.

FIG. 3 is a vertical section view of a test cell of the cartridge shown in FIG. 2, taken substantially in the plane of line 3—3.

FIGS. 4 and 5 are sectional views similar to those shown in FIG. 3, illustrating certain elements of the apparatus and the test cell of the cartridge at the commencement of and during the course of the test involving the condensation of a blood clot.

FIG. 6 is a flow chart of a clot formation and clot condensation test performed preferably using the apparatus shown in FIGS. 2 through 5.

DETAILED DESCRIPTION OF PREFERRED EMBODIMENT

A technique which is used to monitor clot formation of a whole blood or plasma sample may also be used to measure clot characteristics subsequent to clot formation. For example, the copending application for Blood Clot Lysis Measuring Technique describes the measuring of lyric activity in a sample of blood in which clot formation has previously occurred. It has been discovered that if lyric activity is suppressed, the clot will undergo other changes, including condensation.

Clot condensation results in part from the expression of blood serum and other materials which are initially trapped in the intermolecular space between the fibrin polymers in the meshwork of fibrin polymers. After initial clot formation, stronger covalent bonding between the fibrin polymers creates a more tightly bound meshwork of fibrin polymers. The tighter meshwork expresses some of the serum and other materials, and as the serum and other materials are expressed, the fibrin polymers undergo additional, tighter bonding. This process of tighter bonding and additional expression continues until the clot mass consists almost entirely of fibrin polymers, substantially uncontaminated by blood serum and other materials. Clot condensation as described herein may be related to but is not necessarily the same as the activity known as "clot retraction" because of the fluid dynamic effects on the clot as described below.

It has been discovered that clot condensation can be monitored and measured. By measuring clot condensation, the mass of the blood clot can be evaluated. Clot condensation measurements are the basis upon which an index of fibrinogen content of an undiluted blood sample may be evaluated, since the fibrinogen content of the sample is directly related to the mass of fibrin copolymers of the clot. The techniques for measuring the clot condensation and deriving information useful for medical treatment are described below.

Figure 1:
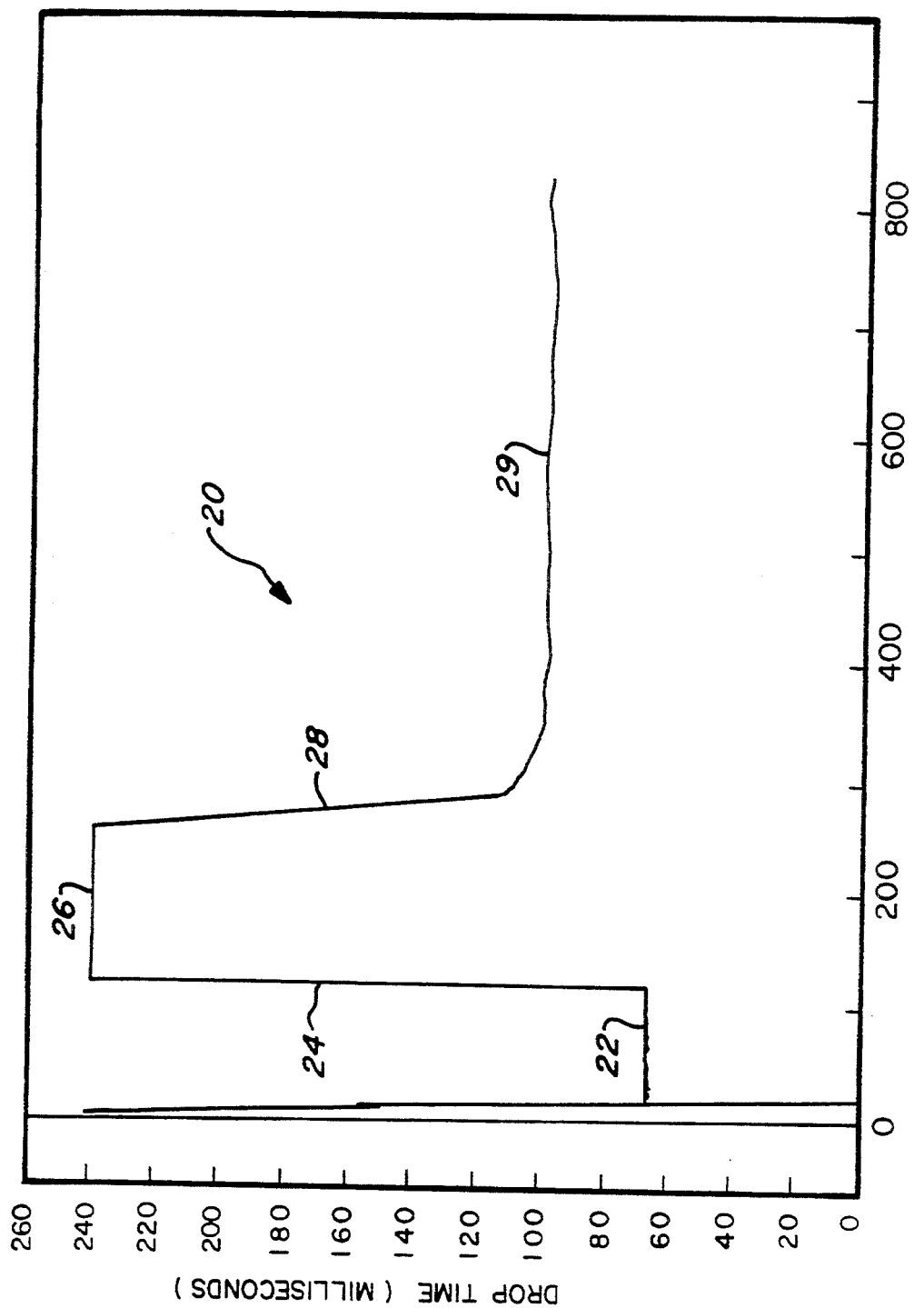
FIG. 1 is a graph containing a single curve which illustrates clot formation and subsequent clot condensation of a clot in a single sample of whole blood or blood plasma.

The measurement of clot formation followed by the measurement of clot condensation of a typical blood sample is illustrated by a graph 20 shown in FIG. 1. The vertical axis indicates the time for a plunger indicator device (described in greater detail below) to drop through the sample, and is generally representative of the clotting or viscosity conditions of the blood sample. The horizontal axis represents the total time in seconds over which the test is run. Thus, curve 20 represents clotting conditions of a sample undergoing clot formation and subsequent clot condensation as measured repeatedly over a period of time sufficient to allow both clot formation and clot condensation to occur.

In vivo, clot formation does not ordinarily transpire in a normal person absent physiological causes such as physical trauma to blood vessels, pathological blood disorders or therapeutically induced blood reactions. Similarly, under in vitro conditions, clot formation may be absent or retarded if the medium or environment into which the blood sample is collected is made of a material which does not stimulate clot formation, such as plastic or siliconized glass. Moreover, even when clot formation has occurred, naturally occurring or therapeutically induced clot lysis may prevent condensation of the clot. Thus, in order to accomplish in vitro measurement of blood clot formation and clot condensation as illustrated in curve 20, additional reagents have been added to the blood sample to induce or maximize clot formation and to prevent clot lysis. These reagents preferably include heparinase, which would be added to inactivate any heparin within the blood sample which might otherwise retard clot formation, an activating reagent such as kaolin to encourage platelet activation and to promote clot formation, and an anti-fibrinolytic reagent to inactivate streptokinase, urokinase or other thrombolytic or fibrinolytic agents which would otherwise foster lysis of the clot.

An initial horizontal component 22 of the curve 20 is the time during which the blood sample is undergoing activities leading to clot formation. During this time, the sample is undergoing mixing of blood and reagents. The mixing promotes contact between blood constituents and reagents. For example, mixing can increase contact between heparinase and heparin, if present, resulting in an increased inactivation of the heparin by the heparinase. Mixing also increases activation of blood constituents such as platelets by the more thorough contact of the blood sample with the activating agent. Platelet activation stimulates the platelets to release activators to further promote clot formation, among other effects. The importance of the initial mixing phase is more completely described in the copending U.S. patent application Ser. No. 07/749,211, noted above.

A nearly vertical component 24 of the curve 20 represents the normal, almost instantaneous increase in indicator drop time resulting from clot formation which causes changes in properties of the sample, typically a marked increase in sample viscosity. The increased viscosity primarily results from the polymerization of fibrinogen monomers into the meshwork of fibrin polymers of increased molecular weight and size in the blood.

The next horizontal component 26 of the curve 20 indicates a time of continued measurements of maximum indicator drop time resulting after the initial clotting of the sample. At this time, condensation of the clot about the indicator is commencing, but its effect is not yet measurable. Although initially immeasurable, clot condensation will eventually result in the compacting of the fibrin polymers which comprise the clot.

A downwardly curving component 28 of the curve 20 represents the period during which indicator drop time is decreasing due to clot condensation. As the clot condenses, the surface area of the clot decreases. As the surface area of the clot decreases, the clot faces less resistance to movement through the fluid of the sample. The decrease in resistance causes the indicator to descent through the fluid faster, which results in a decreased indicator drop time. While coagulation may be almost instantaneous as represented by component 24, the more gradual nature of clot condensation, as represented by the curving component 28, reflects, in part, the more gradual nature of clot condensation. One factor which contributes to the initially slower clot condensation rate as compared to clot formation rate is the initial size of the clot. Initially, the clot forms loosely about the plunger indicator device. The initially formed clot presents a relatively large surface area which slows the descent of the plunger indicator device through the fluid. While the slower descent means the fluid does not contact the descending clot with force sufficient to instantaneously pack the fibrin polymers closely together, extended polymerization causes the clot to become slightly more compact and the surface area of the clot begins to decrease. As the surface area of the clot decreases, resistance to the fluid decreases and the indicator and the clot descend faster through the fluid. The fluid dynamic forces from the increasingly faster descent results in the fluid contacting the moving clot with force sufficient to accelerate or assist in packing the fibrin polymers more tightly. In this way, the clot becomes increasingly condensed.

The final horizontal component 29 of the curve 20 represents a stabilization of the time taken for the indicator and associated clot to descent through the fluid. The stabilized drop time indicates a maximally condensed clot. The drop time stabilizes because clot condensation has essentially ceased. Clot condensation ceases when the intermolecular spaces between the fibrin polymers in the meshwork have been minimized and the fibrin polymers are packed as tightly as possible for the particular characteristics of the blood sample undergoing evaluation. Since a fully condensed blood clot is composed principally of fibrin polymers, the stabilized drop time is related to the clot mass. Also, since all of the fibrinogen in the unclotted blood sample is polymerized into fibrin polymers, the stabilized drop time relates to the fibrinogen content in the previously unclotted sample of blood.

The testing that resulted in the present invention and the practical applications of the present invention are preferably achieved by the use of the assignee's plunger technique apparatus 30 and a plunger sensor cartridge 32 shown generally in FIGS. 2, 3, 4 and 5. Many of the details of the functionality of the apparatus 30 and the cartridge 32 used preferably to perform these tests and to practice the present invention have been generalized, with the understanding that the applicant's prior patents and application disclose these details to a greater extent. See, for example, the applicant's assignee's prior U.S. Pat. Nos. 4,599,219 to Cooper, et al., and U.S. Pat. No. 4,752,449 to Jackson, et al., and U.S. Pat. No. 5,174,961 to Smith.

In general, the cartridge 32, as shown in FIGS. 2, 3, 4 and 5 includes a plurality of test cells 34, each of which is formed generally as a downward extending truncated tube-like member 36. Each of the tube-like members 36 is connected to an upper shelf portion 38. A plunger assembly 40 extends downward from an upper open end of each test cell 34 into the tube-like member 36. Each plunger assembly 40 includes at least one and preferably a pair of flags 42 at its upper end located at a position above the shelf portion 38. The plunger assembly 40 also includes a shaft 46 which extends from the flags 42 downward to a lower end upon which a disk member 48 is attached. The disk member 48 is formed of resilient material and includes an annular flange 50 located above and extending outward from a generally cylindrical main body portion 52. The annular flange 50 includes slots or openings (not shown) formed therein at outer circumferential locations. The plunger assembly 40 functions as the indicator device to determine the clotting conditions of the sample when the cartridge 32 is used with the apparatus 30.

As shown in FIG. 3, prior to using the plunger sensor cartridge 32 in the apparatus 30, the disk member 48 is positioned with its main body portion 52 located in and sealed against an opening 54 formed by a partition 56 extending inwardly from the tube-like member 36. The partition 56 is located between the upper and lower open ends of the tube-like member 36. A resilient flexible plug 58 is positioned in the interior of the tube-like member 36 at its lower open end. A reaction chamber 63 is generally defined by that portion of the open tube-like member 36 above the partition 56. The plug 58 seals against the inner side walls of the tube-like member 36 and confines a quantity of one or more reagents 60 in a reagent chamber 62 between the partition 56 and the plug. The reagents 60 may be a liquid or a solid powder. When more than one reagent 60 is confined in the chamber 62, the reagents are selected to co-exist with one another without adverse influence on the properties of other reagents. When utilizing the apparatus 30 to conduct coagulation and clot condensation tests, an anti-thrombolytic agent is preferably present as a reagent 60 in the reagent chamber 62. As used herein, the term anti-thrombolytic agent may include anti-fibrinolytic agents.

The plunger sensor cartridge 32 is inserted into a receiving block 64 in the apparatus 30 during use, as is shown in FIGS. 2, 4 and 5. Each of the test cells 34 extends into a receptacle 66 of the receiving block 64. Each receptacle 66 has a configuration adapted to receive a test cell 34, while the shelf portion 38 of the cartridge 32 sits on top of the block 64.

The apparatus 30 is generally formed of subassemblies. A plunger lifting subassembly (not fully shown) which includes a lift wire 69 (FIGS. 4 and 5) initially lifts the plunger assembly 40 from its seated position (shown in FIG. 2) and thereafter, releases the plunger assembly and allows it to descend through the liquid in the reaction chamber. The lift wire 69 and the plunger lifting subassembly control the lifting movement of the plunger assembly 40. A reagent drive subassembly (not shown) which includes a plug driver shaft 70, moves the plug 58 to force the reagent 60 into the reaction chamber 63 after the plunger assembly 40 has been removed from its seated position. A dispensing subassembly 72 (FIG. 2) automatically supplies a sample of blood into the reaction chamber 63 of each test cell 34 of the cartridge 32 before the test and prior to the initial movement of the plunger assembly 40 from its seated position. An optical sensing system (not shown) senses the physical descent of the plunger assembly 40 through the mixture in the reaction chamber 63 in order to detect coagulation and clot condensation conditions.

The sample of blood is supplied by the dispensing subassembly 72 to the reaction chamber 63 from a syringe 74 having a blunt needle 76 attached thereto, as shown in FIG. 2. The syringe 74 is manually attached to the dispensing subassembly 72 of the apparatus 30 by a retention device 77. The chamber of the syringe 74 contains blood, preferably fresh drawn from the patient, upon which the coagulation and clot mass measurement testing is to be performed. Of course, prior to attachment of the syringe 74 to the dispensing subassembly 72, all air or other voids in the fluid within the syringe chamber and the blunt needle 76 is removed in a conventional manner. A plunger 78 located within the chamber of the syringe 74 is engaged with a drive wheel 80. Rotation of the drive wheel 80 forces the syringe plunger 78 downward a predetermined amount and thereby expels a predetermined amount of blood from the lower end of the blunt needle 76. The extent to which the syringe plunger 78 is moved downward determines the quantity of fluid expelled from the needle 76.

The dispensing subassembly 72 also includes a movement frame 84 which is moved laterally in the horizontal direction along guide rods 86. The degree of lateral movement is controlled by rotation of a threaded shaft 88 by a microprocessor-controlled motor (not shown) in accordance with programmed information, thereby locating the blunt needle 76 directly above the open upward end of each test cell 34 of the cartridge 32. After attaining the proper lateral location, the movement frame 84 moves the syringe 74 vertically downward to insert the lower end of the blunt needle 76 into the upper open end of each of the test cells 34. The desired amount of fluid sample is automatically dispensed into the reaction chamber 63 of the test cell 34. Thereafter, the blunt needle 76 is withdrawn from the test cell 34 by the dispensing subassembly 72 and is moved to the next lateral position over a test cell 34. The sequence again repeats itself, resulting in the dispensing into the reaction chamber 63 of each test cell 34 of the cartridge 32 that predetermined amount of blood sample needed for conducting the clot mass measurement test.

As shown in FIGS. 3, 4 and 5, the lift wire 69 of the plunger lifting subassembly is initially positioned in a lowermost location, and in that position a horizontal segment of the lift wire fits underneath the flags 42 of the plunger assembly 40. Upward movement of the lift wire 69 lifts each plunger assembly 40 upward, thereby removing the disk member 48 from its seated, sealed location in the opening 54 of the partition 56, of each tube-like member 36 as is shown in FIG. 4. A fluid communication passageway through the opening 54 between the reagent chamber 62 and the reaction chamber 63 is thereby established. Thereafter, or simultaneously with the upward movement of the plunger assembly 40, one of the plurality of plug driver shafts 70 of the reagent drive subassembly moves upward, forcing each plug 58 upward, collapsing the reagent chamber 62 and forcing its contents 60 into the reaction chamber 63. The reagent 60 is thereafter mixed with the fluid sample in the reaction chamber 63 by reciprocating the plunger assembly 40. This condition is illustrated in FIG. 5.

The tube-like member 36 of each test cell 34 is formed of clear material such as plastic, and optical sensors (not shown), which are located within the interior of each receptacle 66 of the receiving block 64, are used for the purpose of monitoring the descent of the plunger assembly 40 relative to the controlled descent or movement of the lift wire 69. In this way, the time which is required for the plunger assembly 40 to drop through the mixture in the reaction chamber 63 is measured during the performance of the tests of the present invention.

A flow chart of a preferred form of a clot mass measurement test 100 is shown in FIG. 6 and will be described as performed in conjunction with the apparatus 30 and cartridge 32 as shown in FIGS. 2, 3, 4 and 5. The steps in the clot mass measurement test 100 will be referred to below by reference numbers enclosed in parentheses. The plunger sensor cartridge 32 is first inserted (102) into the receiving block 64 of the apparatus 30. The syringe 74 which has been previously filled with the blood sample to be tested is then inserted (104) into the sample dispensing subassembly 72 of the apparatus 30. The operator enters any required information utilizing a plurality of control switches 95 (FIG. 2) on the exterior housing of the apparatus 30 and begins the test 100 by activating one of the control switches. A precise predetermined amount of blood is then injected (106) into the reaction chamber 63 of the cell 34 of the cartridge 32, preferably by the dispensing subassembly 72. The blood sample in the reaction chamber 63 is initially kept separate from the reagents 60 in the reagent chamber 62, until the plunger lifting subassembly lifts the plunger assembly 40 and the plug driver shaft 70 forces the plug 58 upward, thereby adding the reagents (108) into the reaction chamber 63 and creating a test mixture of the blood sample and the reagent. In this manner, the blood sample in the reaction chamber 63 is kept separate from an activating reagent 60 in the reagent chamber 62 until the commencement of the test thereby insuring that coagulation and subsequent clot condensation will be consistently measured.

The plunger lifting subassembly lifts the plunger assembly 40 and allows it to descend on a repeating basis, thereby initially reciprocating the plunger assembly (109), to achieve initial mixing of the blood sample and the reagents. This initial mixing has been determined to be important in obtaining precise activated clotting time data, as is described in the aforementioned copending application, Ser. No. 07/749,211. At a predetermined point after which the desired degree of mixing is achieved, clot condensation test steps (110 to 122) commence. The commencement of the clot condensation steps may or may not begin after mixing is complete, but the clot condensation test steps should begin under predetermined repeatable conditions with each test.

Upon commencement of the clot condensation steps, the plunger assembly 40 is lifted and released to drop or descend through the sample fluid in a reciprocative manner (110) by the plunger lifting subassembly. The time taken for the plunger to drop through the fluid is measured (112) by the optical sensing system. The sequence of reciprocating the plunger assembly 40 (110) and measuring the plunger drop time (112) is continuously repeated. Preferably, each plunger drop time measurement is maintained in the memory of the microprocessor or otherwise recorded for subsequent calculations and possible data display purposes, and it is by comparing one or more previous drop times with the currently measured drop time that coagulation and clot condensation are determined.

As the viscosity of the test mixture changes due to clotting, the descent of the plunger assembly 40 slows. Once a change in the drop time of a predetermined magnitude is detected (114), coagulation of the sample is determined to have occurred. This is shown by component 24 of the curve 20 shown in FIG. 1.

After coagulation occurs, the plunger lifting subassembly continues to reciprocate (116) the plunger assembly 40 and plunger drop time is continued to be measured (118). This represented by the component 26 of the curve 20 shown in FIG. 1. Any lysing agents present in the blood will have been deactivated by the anti-fibrinolytic or anti-thrombolytic reagents previously added to the fluid. After coagulation is complete, the clot associated with the reciprocating indicator begins to condense more closely about the indicator. The descent time of the plunger assembly 40 begins to decrease as clot condensation occurs. This condition is illustrated by component 28 of the curve 20 shown in FIG. 1. The reciprocation of the plunger is continued (116), and the drop time is continued to be measured (118). Once it is determined that changes in plunger drop time are minimal or no longer occurring, (component 28 of the curve 20 in FIG. 1), condensation of the coagulated blood sample is determined to have been completed (120). There are a variety of ways to determine whether changes are minimal or no longer occurring, such as calculating the slope of the component 28 of curve 20 in FIG. 1 and determining whether it has reached a predetermined value. Upon detection of the completed clot condensation event, a final drop time is computed (122). The final drop time is the stabilized drop time shown at 29 in FIG. 1, and is indicative of the mass of the condensed clot and the amount of fibrinogen in the sample.

Figure 7:
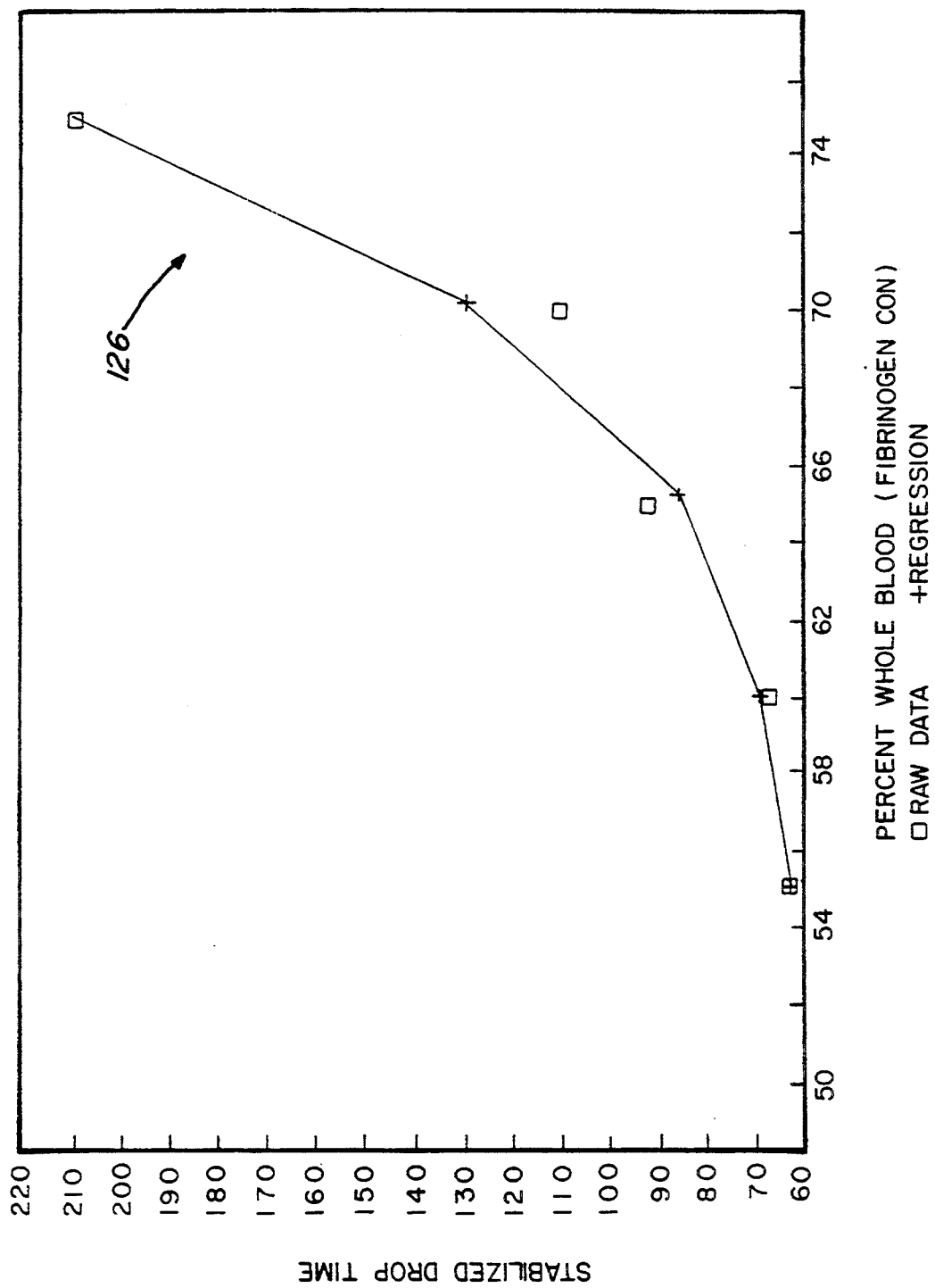
FIG. 7 is a graph containing a single curve which has been derived from the performance of the clot condensation test described in FIG. 6 on a multiplicity of differently diluted samples of whole blood or blood plasma from a single source.

In practicing the clot mass measurement test just described, it has been discovered that the stabilized drop time varies as the blood concentration of the sample is changed. A more concentrated blood sample yields a longer stabilized drop time than the stabilized drop time of a more dilute blood sample. Moreover, it has been discovered that by measuring the stabilized drop times of a multiplicity of samples of different concentrations of blood from a single source and by performing a regression analysis on the resulting stabilized drop times, a curvilinear relationship can be determined. FIG. 7 shows a single curve 126 which is the result of such a regression analysis. The vertical axis of FIG. 7 represents the stabilized drop time for each of the variously diluted samples of blood. The horizontal axis of FIG. 7 represents the dilution factor for each of the variously diluted samples of blood. The correlation between stabilized drop times and the dilutions of a sample of blood as illustrated by the curve 126 represents the continuum of clot mass measurements corresponding to a range of dilutions of the sample of blood.

Since the clot mass also indicates the fibrinogen content of the blood, the correlation illustrated by curve 126 is an indication of the fibrinogen content of the variously diluted samples of blood for which clot mass measurements have been made. An index of fibrinogen content can be determined by obtaining stabilized drop times on a plurality of variously diluted samples of blood from a single source, performing a regression analysis to determine the correlation between the plurality of stabilized drop times (illustrated by curve 126), and calculating the index of fibrinogen content for undiluted blood from the same source as the blood samples tested.

The preferred embodiment of a test which determines the fibrinogen content of blood is performed using an apparatus 30 and a cartridge 32 containing a plurality of cells 34. Prior to performing the clot mass measurement test 100 shown in FIG. 6, predetermined, varying amounts of reagents are placed in the reaction chamber 60 and the reagent chamber 63 of each of the test cells 34. Then each of the cells 34 is supplied with a predetermined measured amount of the same blood sample by the dispensing subassembly 72 of the apparatus 30. The different amounts of reagents previously placed in the reaction chamber 60 and the reagent chamber 63 of each of the plurality of cells 34, create a different concentration or dilution of blood in each cell. As an alternative, different amounts of blood could be mixed with the reagent to also create different concentrations or dilutions of blood. The clot mass measuring test 100 illustrated in FIG. 6 is then performed simultaneously on each of the cells 34. As clot condensation occurs in each of the cells 34, the stabilized drop time for each cell is determined and stored along with a correlated value for the dilution of blood in that cell.

After all stabilized drop times have been determined for all such cells 34, the regression analysis is performed. Based upon the curvilinear relationship determined by the regression analysis (Curve 126, FIG. 7), an index of fibrinogen content for the undiluted blood may be displayed on the face of the apparatus 30. After the relationship is established, that relationship can thereafter be used along with the initial drop time representing the initial clotting (curve portion 26 in FIG. 1) along with the stabilized clotting time to predict the percentage of clottable material or fibrinogen in the blood sample. By determining the difference in the initial clotting drop time and the stabilized clotting time and comparing that to the curve established by the analysis, a measure of the fibrinogen concentration is available. Regression analysis of blood samples obtained from different patients may reveal sufficient similarities in the curve 126 (FIG. 7) among all patients to allow reasonably accurate evaluations of the fibrinogen concentration of any patient using only a generic curve and the specific information regarding the difference in initial clotting time and the stabilized clotting time. If a generic curve is regarded as inapplicable, a specific curve should be derived for each patient prior to medical treatment to be used in later determining fibrinogen concentrations under conditions medical treatment.

From the foregoing description, it can be appreciated that the fibrinogen content of blood can be measured by measuring the clot mass of a fully clotted blood sample which has been allowed to undergo subsequent clot condensation. Moreover, utilization of the apparatus 30 in conjunction with a cartridge 32 and test cells 34 to measure the clot mass of a fully clotted blood sample in which the clot has fully condensed requires a minimum of operator intervention and results in accurate and highly sensitive measurements of fibrinogen content which are quickly derived. Furthermore, fibrinogen content measurements provide information useful in predicting whether an abnormal coagulation condition is related to fibrinogen levels, and thus aids physicians in the diagnosis of blood clotting problems.

Presently preferred embodiments of the present invention and many of its improvements have been described with a degree of particularity. It should be understood that this description has been made by way of preferred example, and that the invention is defined by the scope of the following claims.

What is claimed:

1. A method of evaluating one of a mass attribute of a clot formed from a sample of blood or the fibrinogen content of the clot formed from the sample of blood, comprising the steps of:
    forming a clot in the sample of blood;
    allowing the clot to condense immediately following the formation of the clot;
    moving the clot in the sample during the steps of forming the clot and allowing the clot to condense;
    applying fluid dynamic pressure on the clot during the moving step;
    measuring a predetermined characteristic of the clot related to the volume of the clot when the clot is formed;
    measuring a predetermined characteristic of the clot related to the volume of the clot when the clot is condensed;
    comparing the measured predetermined characteristic at clot condensation relative to the measured predetermined characteristic at clot formation; and
    evaluating one of the mass attribute of the clot or the fibrinogen content from the comparison.

2. A method as defined in claim 1 further comprising the steps of:
    adding the sample of blood to a container; and
    performing the clot forming step and allowing the clot condensing step to occur in the container.

3. A method as defined in claim 2 further comprising the step of:
    mixing the sample of blood with at least one reagent in the container prior to commencing the clot forming step.

4. A method as defined in claim 3 wherein the reagent comprises a clot activating agent.

5. A method as defined in claim 3 wherein the reagent comprises an anti-thrombolytic agent.

6. A method as defined in claim 3 wherein the reagent comprises an agent for deactivating an anticoagulant present in the sample of blood.

7. A method as defined in claim 3 further comprising the steps of:
    mixing a plurality of reagents with the sample of blood, the plurality of reagents including an agent for deactivating an anticoagulant present in the sample of blood, an anti-thrombolytic agent for preventing lysis of the clot and an agent for activating clotting of the sample of blood.

8. A method as defined in claim 1 wherein the fibrinogen content of the blood is evaluated, and said method further comprises the steps of:
    mixing in a first container a first sample of the blood with a reagent;
    mixing in a second container a second sample of the blood with a reagent;
    creating different predetermined concentrations of the blood in the first and second samples by adjusting the quantities of the blood and reagent mixed in the first and second samples;
    performing the steps of forming the clot, allowing the clot to condense and measuring the predetermined characteristic with respect to the clots formed from each of the first and second samples after the different concentrations have been established; and
    utilizing the measurements of the predetermined characteristics of the clots formed from the first and second samples to evaluate the fibrinogen content of the blood.

9. A method as defined in claim 8 wherein the step of utilizing the measurements of the predetermined characteristics of the clots formed from the first and second samples to evaluate the fibrinogen content further comprises the steps of:
    deriving a mathematical expression which describes the relationship between the measurements of the predetermined characteristics of the clots formed from the first and second samples.

10. A method as defined in claim 9, further comprising the steps of:
    reciprocating an indicator device in each sample by raising the indicator device and allowing the indicator device to descend into each sample;
    repeatedly reciprocating each indicator device in each sample;
    forming the clot on the indicator device and allowing the clot to condense on the indicator device while reciprocating the indicator device in each sample;
    applying fluid dynamic pressure on each clot during condensation by allowing the indicator device upon which the clot is formed to descend into each sample;
    determining a drop time for the indicator device upon which the clot is formed to descend into the sample; and
    measuring the predetermined characteristic of each clot by determining the drop time of the indicator device.

11. A method as defined in claim 10 further comprising the steps of:
    determining an initial drop time for the indicator device when the clot is initially formed on the indicator device;
    determining a stabilized drop time for the indicator device upon which the condensed clot is formed after the condensation of the clot has occurred to a predetermined amount;
    determining the difference in time between the initial descent time and the stabilized descent time; and
    predicting the fibrinogen content of the blood by application of the difference in time to the mathematical expression.

12. A method as defined in claim 1 wherein the measuring step further comprises:

repeatedly reciprocating an indicator device in the sample;

allowing the indicator device to descend into the sample during each reciprocation;

forming the clot on the indicator device and allowing the clot to condense on the indicator device while reciprocating the indicator device in the sample;

measuring a drop time of the indicator device to descend into the sample;

measuring the drop time of the indicator device upon initially forming of the clot; and subsequently measuring the drop time of the indicator device upon achieving maximum stabilized condensation of the clot.

13. A method as defined in claim 12 wherein the indicator device is a plunger; the sample is added to a test cell; the test cell comprises a reagent chamber, a reaction chamber, and a displaceable sealing member connected to the indicator device and initially positioned between the reagent and reaction chambers; and the steps of forming the clot, allowing the clot to condense and measuring the predetermined characteristic are performed in the reaction chamber.

14. A method as defined in claim 1 further comprising the steps of:

applying fluid dynamic forces on the clot during condensation by moving the clot in the sample.

15. A method as defined in claim 14 further comprising the steps of:

accelerating the condensation of the clot by applying the fluid dynamic forces on the clot.

16. A method as defined in claim 1 further comprising the steps of:

measuring the predetermined characteristic while applying fluid dynamic forces to the clot by moving the clot in the sample while allowing the clot to condense, 17. A method as defined in claim 1 further comprising the steps of:

measuring the time for the clot to form;

measuring the time for the clot to condense after the clot is formed; and wherein the step of comparing the predetermined characteristics further comprises the step of:

comparing the times measured for the clot to form and the clot to condense.

18. A method as defined in claim 1 further comprising the steps of:

moving a device in the sample;

forming the clot on the device;

allowing the clot to condense on the device;

repeatedly allowing the device and the clot formed on the device to descend through the sample during clot formation and clot condensation;

measuring a drop time for the device and the clot formed on the device to descend into the sample;

determining clot formation by detecting a change in the drop time of the device and the clot formed on the device;

determining clot condensation by detecting a change in the drop time of the device and the clot formed on the device after the clot has formed;

using the measured drop times of the device and the clot formed on the device at clot formation and at clot condensation to establish the predetermined characteristic.

* * * * *